United States Patent
Animati et al.

(10) Patent No.: US 6,653,289 B1
(45) Date of Patent: Nov. 25, 2003

(54) L-ARABINO-DISACCHARIDES OF ANTHRACYCLINES, PROCESSES FOR THEIR PREPARATION, AND PHARMACEUTICAL COMPOSITIONS CONTAINING THEM

(75) Inventors: Fabio Animati, Rome (IT); Marco Berettoni, Rome (IT); Mario Bigioni, Rome (IT); Amalia Cipollone, Rome (IT); Carlo Alberto Maggi, Florence (IT)

(73) Assignee: Menarini Ricerche S.p.A., Pomezia (IT)

( * ) Notice: Subject to any disclaimer, the term of this patent is extended or adjusted under 35 U.S.C. 154(b) by 0 days.

(21) Appl. No.: 09/914,987

(22) PCT Filed: Mar. 8, 2000

(86) PCT No.: PCT/EP00/02006

§ 371 (c)(1),
(2), (4) Date: Dec. 18, 2001

(87) PCT Pub. No.: WO00/53615

PCT Pub. Date: Sep. 14, 2000

(30) Foreign Application Priority Data

Mar. 9, 1999 (IT) ......................... FI99A0043

(51) Int. Cl.$^7$ ......................... A61K 31/70; C07H 15/24
(52) U.S. Cl. ......................... 514/34; 536/6.4; 536/18.5; 536/18.6
(58) Field of Search ......................... 536/4.1, 6.4, 16.8, 536/17.2, 18.1, 18.3, 18.5, 18.6; 514/25, 33, 34, 35

(56) References Cited

FOREIGN PATENT DOCUMENTS

WO    WO 95/09173    4/1995

OTHER PUBLICATIONS

Danesi, Romano, et al., "Measurement of the SαT Segment as the Most Reliable Electrocardiogram Parameter for the Assessment of Adriamycin–Induced Cardiotoxicity in the Rat," *Journal of Pharmacological Methods,* vol. 16, pp. 251–259, 1986.

Villani, Fabrizio, et al., "Relationship Between Doxorubicin–Induced ECG Changes And Myocardial Alterations In Rats," *Tumori,* vol. 72, pp. 323–329, 1986.

Jensen, R.A., et al., "Doxorubicin Cardiotoxicity in the Rat: Comparison of Electrocardiogram, Transmembrane Potential, and Structural Effects," *Journal of Cardiovascular Pharmacology,* vol. 6, pp. 186–200, 1984.

Arcamone, Federico, "Doxorubicin:Anticancer Antibiotics" *Academic Press,* pp. 243–245, 1981.

Animati et al, "New anthracycline disaccharides. Synthesis of L–daunosaminyl–α(1→4)–2–deoxy–L–rhamnosyl and of L–daunosaminyl–α(1→4)–2–deoxy–L–fucosyl daunorubicin analogues", J. Chem Soc. Perkin Trans. 1, 1996, Apr. 25, 1996.

*Primary Examiner*—James O. Wilson
*Assistant Examiner*—Josephine Young
(74) *Attorney, Agent, or Firm*—Morgan & Finnegan LLP

(57) ABSTRACT

The present invention refers to compounds of general formula (I), the pharmaceutically acceptable salts thereof, the processes for their preparation, and the pharmaceutical compositions containing them.

7 Claims, No Drawings

L-ARABINO-DISACCHARIDES OF ANTHRACYCLINES, PROCESSES FOR THEIR PREPARATION, AND PHARMACEUTICAL COMPOSITIONS CONTAINING THEM

FIELD OF THE INVENTION

The present invention refers to compounds of general formula (I)

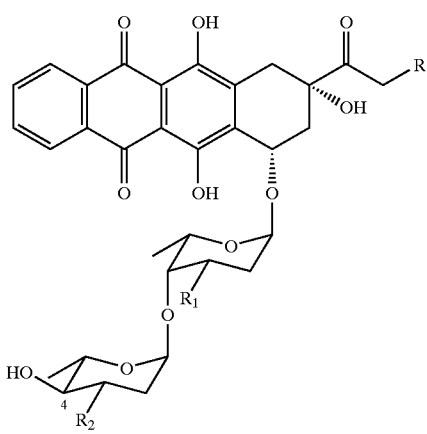

and pharmaceutically acceptable salts thereof having anticancer properties, where R is OH;

$R_1$ is H or OH;

$R_2$ is H or OH or $NH_2$.

The present invention also refers to the processes for the preparation of said compounds, their pharmaceutically acceptable salts, and the pharmaceutical compositions containing them.

PRIOR ART

Daunorubicin and doxorubicin are established anticancer drugs currently used in the clinical practice for the treatment of a variety of solid tumours and leukaemia (F. Arcamone in "Doxorubicin: Anticancer Antibiotics", Academic Press, N.Y., 1981).

It is however known that the severe side effects (first of all, chronic cardiotoxicity and secondly acute myelosuppression) caused by said antibiotics and the other anthracyclines used at present impose limits on the use of same in a large number of patients who, otherwise, would benefit from the treatment. Said side effects, in fact, set a limit to the maximum administrable dose and to the number of treatment cycles.

Therefore, there is an urgent need for the coming onto the market of drugs highly selective in their inhibitory action against the proliferation of diseased cells in respect of the normal ones, and characterised by a lower cardiotoxicity, which would allow their use in higher doses as well as the achievement of increased therapeutic indices.

It is an object of the present invention to provide new anticancer drugs, in particular anthracycline analogues, in which the carbohydrate portion consists of a disaccharide residue.

In general, in the known natural or synthetic anthracyclines with anticancer activity, which contain two or more carbohydrate residues, the sugar directly bound to aglycone always contains a free or substituted amino group.

A recent industrial invention (WO 95/09173) refers to anthracyclines with a disaccharide residue, in which the sugar directly bound to aglycone never contains amino groups.

DETAILED DESCRIPTION OF THE INVENTION

The anthracyclines being the object of the present invention always contain an L-arabino group, or an amino derivative thereof, in the disaccharide portion, and said arabino group is always the furthest sugar from the aglycone bond.

Furthermore, unlike most active anthracyclines containing two or more carbohydrate residues, the sugar directly bound to aglycone never contains an amino group.

For facility of understanding, it is worth noting that in the present invention the substituents of the disaccharide group, defined in WO 95/09173 as $R_3$, $R_4$ and $R_5$, are all in equatorial position and the group defined therein as $R_5$ is always a hydroxyl group. The equatorial position of the hydroxyl group in position 4 on the second sugar of the compounds of general formula (I) is of particular importance to the present invention.

It has surprisingly been found that, compared with the anthracycline disaccharides described in WO 95/09173, which contain the hydroxyl group in position 4 on the second sugar in axial position [see general formula (I)], the anthracyclines of the present invention are characterised by a higher anticancer activity and selectivity as well as by a lower cardiotoxicity. The decrease in cardiotoxicity could not be expected to exclusively depend on the presence of said hydroxyl group in the carbohydrate residue.

The compounds of the present invention are the compounds of general formula (I), as reported above, and their pharmaceutically acceptable salts, in which R, $R_1$, $R_2$ are as described above.

The invention also refers to pharmaceutical compositions containing the aforementioned compounds or salts thereof with pharmaceutically acceptable acids, preferably the hydrochloric acid.

Particularly preferred are the following compounds:

a) 7-O-[2,6-dideoxy-4-O-(2,3,6-trideoxy-3-amino-α-L-arabino-hexopyranosyl)-α-L-lyxo-hexopyranosyl ]-4-demethoxy-doxorubicinone chlorhydrate (R=$R_1$=OH, $R_2$=$NH_2$);

b) 7-O-[2,3,6-trideoxy-4-O-(2,3,6-trideoxy-3-amino-α-L-arabino-hexopyranosyl)-α-L-lyxo-hexopyranosyl ]-4-demethoxy-doxorubicinone chlorhydrate (R=OH, $R_1$=H, $R_2$=$NH_2$);

c) 7-O-[2,6-dideoxy4-O-(2,6-dideoxy-α-L-arabino-hexopyranosyl)-α-L-lyxo-hexopyranosyl ]-4-demethoxy-doxorubicinone chlorhydrate (R=$R_1$=$R_2$=OH);

d) 7-O-[2,3,6-trideoxy-4-O-(2,6-dideoxy-α-L-arabino-hexopyranosyl)-α-L-lyxo-hexopyranosyl ]4-demethoxy-doxorubicinone chlorhydrate (R=$R_2$=OH, $R_1$=H).

The compounds of general formula (I) can be prepared on the basis of a process consisting in the following steps:

a) condensation of a compound of formula (II)

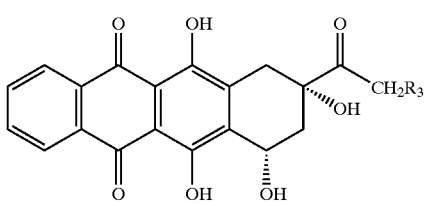

where R₃ is the OR₄ group, in which R₄ is a protective group for an alcoholic function, preferably selected among the acetyl-, chloroacetyl-, dimethylterbutylsilyl or p-methoxyphenyidiphenylmethyl- groups, with a compound of formula (111)

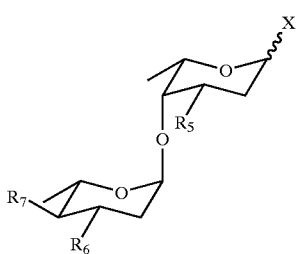

where $R_5$ is H or a protected —OH group, preferably p-nitrobenzoate or allyloxycarbonate; $R_6$ is a H group or a protected —OH group, preferably p-nitrobenzoate or allyloxycarbonate or a protected $NH_2$ group, preferably trifluoroacetamide or allylcarboxyamide; $R_7$ is a protected —OH group, preferably p-nitrobenzoate or allyloxycarbonate, and X is a group capable of generating, under the condensation conditions, a stable carbo-cation that can bind itself to a hydroxyl group in position C-7 of the compound of formula (II), said group X being conveniently selected among the groups used in the glycosidation reaction, e.g. a halogen such as chlorine or bromine, preferably chlorine, or a p-nitrobenzoyloxy group or a thiophenyl or thioethyl group, preferably thiophenyl. Compounds of formula (IV) are thus obtained:

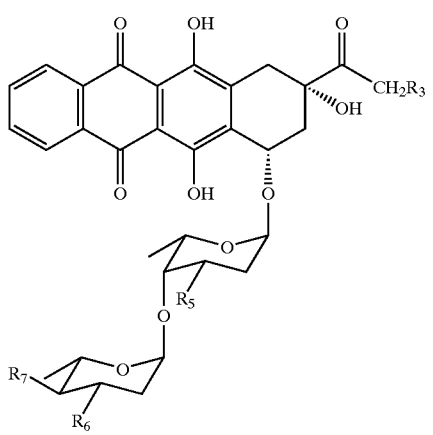

where $R_3$, $R_5$, $R_6$, $R_7$ are as defined above;
b) one or more removal reaction/s of protective groups of OH and/or $NH_2$ functions from compounds of formula (IV) to give compounds of formula (I), where R, $R_1$, $R_2$ are as defined above;

c) conversion, if any, of the aforesaid glycosides of formula (I) into a pharmaceutically acceptable salt thereof, preferably chlorhydrate.

The reaction conditions for the glycosidation of a compound of formula (II) with a compound of formula (III) to give a compound of formula (IV) may vary depending on the type of substituents present in the compounds of formula (III).

Alternatively, if so desired, anthracycline glycosides of formula (I), where $R_1$, $R_2$ are as defined above, and R is an OH group, can be prepared from glycosides of formula (I) or from pharmaceutically acceptable salts thereof, where $R_1$, $R_2$ are as defined above, and R is H, by bromination of the carbon in position 14 with bromine in chloroform followed by hydrolysis, at room temperature for 48 hrs, of the resulting 14-bromo derivatives with sodium formate.

The sequence of reactions giving the compounds of general formula (I) is carried out according to methods already described in literature (see e.g. WO 95/09173) and, therefore, are already known in the art.

The present invention also refers to pharmaceutical compositions containing, as active ingredient, a compound of formula (I) or a pharmaceutically acceptable salt thereof combined with a pharmaceutically acceptable diluent or carrier.

According to the present invention, a therapeutically effective dose of a compound of formula (I) is combined with an inert carrier.

The compositions can be formulated by conventional methods using common carriers.

The claimed compounds are useful for the therapeutic treatment on humans and other mammals. In particular, said compounds are efficacious anticancer agents when administered in therapeutically effective doses.

The activity of a compound representative of formula (I) was evaluated by comparing its cytotoxicity in vitro with the cytotoxicity of compound 7-O-[2,6-dideoxy-4-O-(2,3,6-trideoxy-3-amino-α-L-lyxo-hexopyranosyl)-α-L-lyxo-hexopyranosyl ]-4-demethoxy-doxorubicinone chlorhydrate of general formula (V)

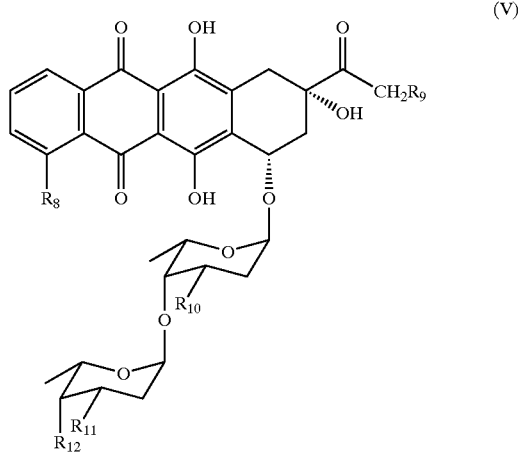

($R_8$=H, $R_9$=$R_{10}$=$R_{12}$=OH, $R_{11}$=$NH_2$) described in patent application WO 95/09173 on lines H460 (pulmonary carcinoma) and GLC-4 (pulmonary microcarcinoma).

The results obtained are shown in Table 1, which reports the concentration (in nmoles) necessary for obtaining a 50% inhibition of diseased cells growth after a 24-h exposure to the drug ($IC_{50}$, nM), with regard to compound (Ia) 7-O-[2, 6-dideoxy-4-O-(2,3,6trideoxy-3-amino-α-L-arabinohexopyranosyl)-α-L-lyxo-hexopyranosyl ]-4-demethoxy-doxorubicinone chlorhydrate (compound of formula (I), R=R$_1$=OH, R$_2$=NH$_2$):

TABLE 1

|    | H460 | GLC-4 |
|----|------|-------|
| V  | 14   | 55    |
| Ia | 10   | 11    |

The activity in vivo of (Ia), compared with that of (V), was also evaluated on a human tumour line implanted s.c. in naked mice (pulmonary microcytoma GLC-4) after administration of 6 mg/kg of drug every 3–4 days, for 5 treatment cycles.

The results obtained are shown in Table 2, which reports the Tumour Weight Inhibition % (TWI% determined 7–10 days after the last treatment) and the Log Cell Kill [LCK in animals treated according to the formula: T-C/DT×3.32, where T and C are the days that tumours take to reach the significant weight fixed in each test. in treated animals (T) and in controls (C)].

TABLE 2

|          | Dose (mg/kg) | | TWI %    |     |
|----------|--------|-------|----------|-----|
| Compound | single | total | (300 mg) | LCK |
| V        | 6      | 30    | 60       | 0.4 |
| Ia       | 6      | 30    | 93       | 1.1 |

The compounds of formula (I) proved to be less cardiotoxic than the compounds of formula (V). Their cardiotoxicity was determined by electrocardiographic analysis of parameters such as QaT, SaT and QRS, 3 days, 4 weeks and 13 weeks, respectively, after the last treatment. Said parameters can be correlated with cardiotoxicity, as disclosed in J. Pharmacol. Meth., 16, 251 (1986); J. Cardiovasc. Pharmacol., 6, 186 (1984); Tumori, 72, 323 (1986).

The results obtained with compound (Ia), 7-O-[2,6-dideoxy-4-O-(2,3,6-trideoxy-3-amino-α-L-arabino-hexopyranosyl)-α-L-lyxo-hexopyranosyl]-4-demethoxy-doxorubicinone chlorhydrate (compound of formula (I), R=R$_1$=OH, R$_2$=NH$_2$) are illustrated in Table 3.

TABLE 3

|                     | Control | V    | Ia   |
|---------------------|---------|------|------|
| QaT duration (msec) |         |      |      |
| 3 days              | 28      | 35   | 30   |
| 4 weeks             | 30      | 42   | 31   |
| 13 weeks            | 30      | 47   | 34   |
| SaT duration (msec) |         |      |      |
| 3 days              | 14      | 20   | 16   |
| 4 weeks             | 16      | 24   | 17   |
| 13 weeks            | 16      | 29   | 20   |
| QRS duration (msec) |         |      |      |
| 3 days              | 18      | 26   | 19   |
| 4 weeks             | 20      | 26   | 19   |
| 13 weeks            | 21      | 31   | 24   |
| QRS voltage (mvolt) |         |      |      |
| 3 days              | 0.48    | 0.58 | 0.50 |
| 4 weeks             | 0.46    | 0.56 | 0.43 |
| 13 weeks            | 0.45    | 0.48 | 0.41 |

The following examples illustrate the present invention in more detail.

Example 1

7-O-[2,6-dideoxy-4-O-(2,3,6-trideoxy-3-amino-α-L-arabino-hexopyranosyl)-α-L-lyxo-hexopyranosyl ]-4-demethoxy-doxorubicinone chlorhydrate (compound of formula (I), R=R$_1$=OH, R$_2$=NH$_2$).

A mixture of protected 4-demethoxy-doxorubicinone (compound of formula (II), R$_3$=OR$_4$, where R$_4$=acetyl) (210 mg, 0.5 mmoles) and 2,6-dideoxy-4-O-(2,3,6-trideoxy-4-O-allyloxycarbonate-3-allylcarboxyamide-α-L-arabino-hexopyranosyl)-3-O-allyloxycarbonate-α-L-lyxo-hexopyranosyl-p-nitrobenzoate (compound of formula (III), R$_5$=R$_7$=allyloxycarbonate, R$_6$=allylcarboxyamide, X=p-nitrobenzoyloxy) (407 mg, 0.6 mmoles) in 36 ml methylene chloride and 12 ml ethyl ether, in the presence of molecular sieves at −20° C., was treated with 201 ml (0.9 mmoles) trimethylsilylfluoromethanesulfonate. The reaction mixture was allowed to stir for 1 hr, diluted with methylene chloride, washed with a saturated solution of sodium bicarbonate and evaporated to dryness. The residue was chromatographed on silica gel (eluent CH$_2$Cl$_2$-EtOH, 96/4) yielding 220 mg of protected 7-O-[2,6-dideoxy-4-O-(2,3,6-trideoxy-4-O-allyloxycarbonate-3-allylcarboxyamide-α-L-arabino-hexopyranosyl)-3-O-allyloxycarbonatea-α-L-lyxo-hexopyranosyl]4-demethoxy-doxorubicinone chlorhydrate (compound of formula (IV), R$_3$=OR$_4$, where R$_4$=acetyl, R$_5$=R$_7$=allyloxycarbonate, R$_6$=allylcarboxyamide).

A protected glycoside solution of the compound of formula (IV) (R$_3$=OR$_4$, where R$_4$=acetyl, R$_5$=R$_7$=allyloxycarbonate, R$_6$=allylcarboxyamide), (215 mg, 0.23 mmoles) in methylene chloride (5 ml) and methanol (10 ml) was treated 1 hr at −10° C. with a 0.5M potassium carbonate solution (0.7 ml). The reaction mixture was neutralised with 0.1N HCl, diluted with methylene chloride, washed with a saturated sodium chloride solution and evaporated to dryness. The residue was separated by preparative HPLC (Merck column RP-18, H$_2$O+0.1% trifluoroacetic acid=60%, CH$_2$CN+0.1% trifluoroacetic acid=40%). The fractions were diluted with AcOEt and treated with a saturated sodium bicarbonate solution. The organic phase separated was washed with water and concentrated under vacuum to yield 144 mg of 7-O-[2,6-dideoxy-4-O-(2,3,6-trideoxy-4-O-allyloxycarbonate-3-allylcarboxyamide-α-L-arabino-hexopyranosyl)-3-O-allyloxycarbonate-α-L-lyxo-hexopyranosyl ]-4-demethoxy-doxorubicinone (compound of formula (IV), R$_3$=OH, R$_5$=R$_7$=allyloxycarbonate, R$_6$=allylcarboxyamide).

A protected glycoside solution of the compound of formula (IV) (R$_3$ =OH, R$_5$=R$_7$=allyloxycarbonate, R$_6$=allylcarboxyamide) (140 mg, 0.156 mmoles) in methylene chloride (20 ml) was treated 15 min in the dark, at room temperature, with N,N-dimethyl-trimethylsilylamine (175 ml, 1.1 mmoles), trimethylsilylacetate (165 ml, 1.1 mmoles) and tetrakis(triphenylphosphine) palladium (0) (9 mg, 00.8 mmoles).

The mixture was diluted with CH$_2$Cl$_2$ and washed with a 2% sodium chloride solution. The organic phase was dried over sodium sulphate and concentrated under vacuum. The residue was added with HCl aqueous solution (pH=3.75). The acid aqueous solution was washed with AcOEt and freeze-dried to give 80 mg of the desired product (compound of formula (I), R=R$_1$=OH, R$_2$=NH$_2$). Yield 75%.

$^1$H-NMR (DMSO-d$_6$), d: 1.15 (d, 3H, CH$_3$"); 1.2 (d, 3H, CH$_3$'); 1.6–1.85 (m, 3H, H-2' ax, H-2' eq and H-2" eq); 2.1 (m, 3H, H-8 ax, H-8 eq and H-2" ax); 3.0 (bb, 3H, H-10 ax, H-10 eq and H-4"); 3.25 (m, 1H, H-3"); 3.6 (bs, 1H, H-4'); 3.85 (m, 1H, H-3'); 4.15 (q, 1H, H-5'); 4.2 (m, 1H, H-5"); 4.6

(d, 2H, H-14); 4.65 (d, 1H, OH-3'); 4.85 (t, 1H, OH-14); 4.95 (bs, 1H, H-1"); 5.0 (bs, 1H, H-7); 5.3 (d, 1H, H-1'); 5.5 (s, 1H, OH-9); 5.6 (d, 1H, OH-4"); 8.0 and 8.3 (two m, 4H, aromatic).

The following compounds of formula (I) have been obtained by an analogous procedure based on glycosidation, deprotection and formation of the final chlorhydrate.

Example 2

7-O-[2,3,6-trideoxy-4-O-(2,3,6-trideoxy-3-amino-α-L-arabino-hexopyranosyl)-α-L-lyxo-hexopyranosyl ]-4-demethoxy-doxorubicinone chlorhydrate (R=OH, $R_1$=H, $R_2$=NH$_2$), by condensation of protected 4-demethoxy-doxonubicinone (compound of formula (II), $R_3$=OR$_4$, where $R_4$=acetyl) with 2,3,6-trideoxy-4-O-(2,3,6-trideoxy-4-O-allyloxycarbonate-3-allylcarboxyamide-α-L-arabino-hexopyranosyl)-α-L-lyxo-hexopyranosyl-p-nitrobenzoate (compound of formula (III), $R_5$=H, $R_6$=allylcarboxyamide, $R_7$=allyloxycarbonate, X=p-nitrobenzoyloxy).

$^1$H-NMR (DMSO-d$_6$), d: 1.1 (d, 3H, CH$_3$"); 1.15 (d, 3H, CH$_3$'); 1.45–1.9 (m, 5H, H-2' ax, H-2' eq, H-2" eq, H-3' eq); 2.1–2.25 (m, 3H, H-8 ax, H-8 eq and H-2' ax); 3.0 (s, 2H, H-10 ax and H-10 eq); 3.15 (m, 1H, H-4"); 3.25 (m, 1H, H-3"); 3.55 (s, 1H, H-4'); 3.65 (m, 1H, H-5"); 4.15 (q, 1H, H-5'); 4.65 (d, 2H, H-14); 4.8 (t, 1H, OH-14); 4.85 (bs, 1 H, H-1"); 5.0 (bs, 1H, H-7); 5.25 (s, 1H, H-1'); 5.5 (s, 1H, OH-9); 5.65 (d, 1H, OH4"); 8.0 (two m, 4H, aromatic).

Example 3

7-O-[2,6-dideoxy-4-O-(2,6-dideoxy-α-L-arabino-hexopyranosyl)-α-L-lyxo-hexopyranosyl ]-4-demethoxy-doxorubicinone chlorhydrate (R=$R_1$=$R_2$=OH), by condensation of protected 4-demethoxy-doxorubicinone (compound of formula (II), $R_3$=OR$_4$, where $R_4$=acetyl) with 2,6-dideoxy-4-O-(2,6-dideoxy-3,4-di-O-allyloxycarbonate-α-L-arabino-hexopyranosyl)-3-O-allyloxycarbonate-α-L-lyxo-hexopyranosyl-p-nitrobenzoate (compound of formula (III), $R_5$=$R_6$=$R_7$=allyloxycarbonate, X=p-nitrobenzoyloxy).

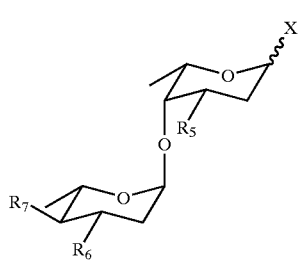

(III)

where $R_5$ is H or a protected —OH group; $R_6$ is a H group or a protected —OH group or a protected NH$_2$ group; $R_7$ is a protected —OH group, and X is a group selected among a halogen or a p-nitrobenzoyloxy- or a thiophenyl group, giving compounds of formula (IV):

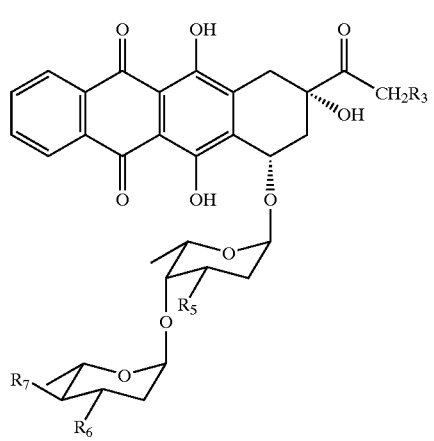

(IV)

where $R_3$, $R_5$, $R_6$, $R_7$ are as defined above;
i) one or more removal reaction/s of protective groups of OH and/or NH$_2$ functions from compounds of formula (IV) giving compounds of formula (I), where R, $R_1$, $R_2$ are as defined above;

What is claimed is:
1. A compound of general formula (I)

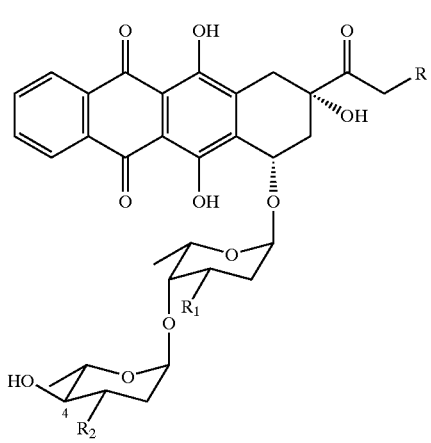

(I)

and pharmaceutically acceptable salts thereof,
where
R is OH;
$R_1$ is H or OH; and
$R_2$ is H or OH or NH$_2$.
2. A compound of formula (I) as claimed in claim 1, selected from the group consisting of
  i) 7-O-[2,6-dideoxy-4-O-(2,3,6-trideoxy-3-amino-α-L-arabino-hexopyranosyl)-α-L-lyxo-hexopyranosyl ]-4-demethoxy-doxorubicinone hydrochloride (R=$R_1$=OH, $R_2$=NH$_2$);
  ii) 7-O-[2,3,6-trideoxy-4-O-(2,3,6-trideoxy-3-amino-α-L-arabino-hexopyranosyl)-α-L-lyxo-hexopyranosyl ]-4-demethoxy-doxorubicinone hydrochloride (R=OH, $R_1$=H, $R_2$=NH$_2$);
  iii) 7-O-[2,6-dideoxy-4-O-(2,6-dideoxy-α-L-arabino-hexopyranosyl)-α-L-lyxo-hexopyranosyl ]-4-demethoxy-doxorubicinone hydrochloride (R=$R_1$=$R_2$=OH);
  iv) 7-O-[2,3,6-trideoxy-4-O-(2,6-dideoxy-α-L-arabino-hexopyranosyl)-α-L-lyxo-hexopyranosyl ]-4-demethoxy-doxorubicinone hydrochloride (R=$R_2$=OH, $R_1$=H).

3. A process for the preparation of a compound of general formula (I)

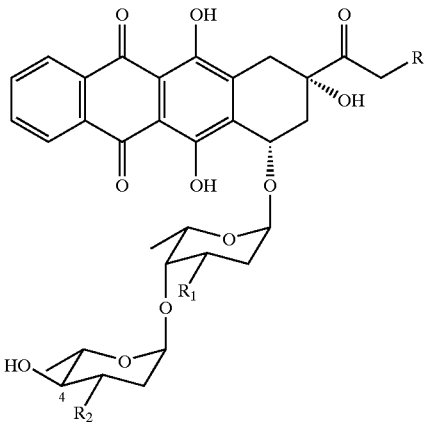

where
R is OH;
$R_1$ is H or OH; and
$R_2$ is H or OH or $NH_2$
or a pharmaceutically acceptable salt thereof, consisting in the following steps:
i) condensation of a compound of formula (II)

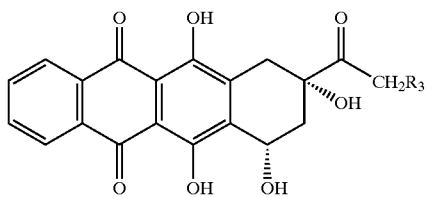

where $R_3$ is the $OR_4$ group, in which $R_4$ is a protective group for an alcoholic function, selected from the group consisting of acetyl, dimethyl-tert-butylsilyl or p-methoxyphenyldiphenylmethyl, with a compound of formula (III)

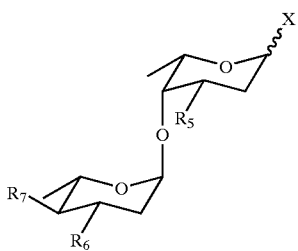

where $R_5$ is H or a protected —OH group; $R_6$ is H or a protected —OH group or a protected $NH_2$ group; $R_7$ is a protected —OH group, and X is a group selected from the group consisting of halogen, p-nitrobenzoyloxy, or thiophenyl, giving compounds of formula (IV):

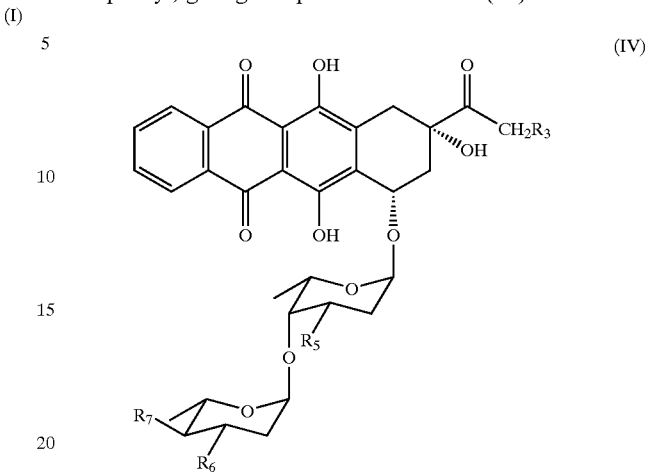

where $R_3$, $R_5$, $R_6$, $R_7$ are as defined above;
ii) one or more removal reactions of protective groups of OH and/or $NH_2$ functions from compounds of formula (IV) giving compounds of formula (I), where R, $R_1$, $R_2$ are as defined above; and
iii) conversion, if any, of the compounds of formula (I) into a pharmaceutically acceptable salt thereof.

4. The process for the preparation of compounds of formula (I) as claimed in claim 1, where $R_1$ and $R_2$ are as defined above and R is the OH group, or their pharmaceutically acceptable salts, consisting in the following steps:
i) bromination of the carbon in position 14 of compounds of formula (I) or their pharmaceutically acceptable salts, where $R_1$ and $R_2$ are as defined above and R is H; and
ii) hydrolysis of the resulting 14-bromo-derivatives to give codmpounds of formula (I), where $R_1$ and $R_2$ are as defined above and R is the OH group.

5. A pharmaceutical composition containing as active ingredient at least one compound of general formula (I) as claimed in claim 1, or a pharmaceutically acceptable salt thereof, combined with a pharmaceutically acceptable diluent or carrier.

6. A pharmaceutical composition containing as active ingredient at least one compound of general formula (I) as claimed in claim 2, or a pharmaceutically acceptable salt thereof, combined with a pharmaceutically acceptable diluent or carrier.

7. A method for the therapeutic treatment of solid tumors and leukaemia in humans wherein therapeutically effective amounts of a compound of formula (I) according to claim 1 is administered to the patient.

* * * * *